United States Patent [19]

Martinez

[11] Patent Number: 4,924,894
[45] Date of Patent: May 15, 1990

[54] LEISURE BELOW BENT KNEE PYLON FOR AMPUTEE

[76] Inventor: Michael M. Martinez, 1223 E. Yandell Dr., El Paso, Tex. 79902

[21] Appl. No.: 362,278

[22] Filed: Jun. 6, 1989

[51] Int. Cl.⁵ .............................................. A61H 3/02
[52] U.S. Cl. ......................................... 135/65; 135/68
[58] Field of Search .................................... 135/65, 68

[56] References Cited

U.S. PATENT DOCUMENTS

| | | | |
|---|---|---|---|
| 875,482 | 12/1907 | Wyatt | 135/68 |
| 1,769,167 | 7/1930 | Scheihing | 135/68 |
| 2,678,054 | 5/1954 | Bostelman | 135/68 |
| 2,778,370 | 1/1957 | Chamble | 135/68 |
| 3,016,060 | 1/1962 | Beattie, Sr. | 135/73 |
| 4,141,375 | 2/1979 | Tykwinski | 135/66 |
| 4,254,948 | 3/1981 | Jacobs | 135/68 |
| 4,291,715 | 9/1981 | Monte | 135/68 |
| 4,793,370 | 12/1988 | Perez et al. | 135/68 |

FOREIGN PATENT DOCUMENTS 118989 6/1947 Sweden .................................. 135/49

Primary Examiner—Carl D. Friedman
Assistant Examiner—Caroline D. Dennison
Attorney, Agent, or Firm—Richard C. Litman

[57] ABSTRACT

A temporary pylon that does not require the use of crutches. A wearer's knee and thigh are secured between two frame supports. Tubing extends below the support frame to allow the wearer to stand. A waist belt pivotably attached to the outer frame member secures the device to the wearer's body.

6 Claims, 1 Drawing Sheet

LEISURE BELOW BENT KNEE PYLON FOR AMPUTEE

BACKGROUND OF THE INVENTION

1. Field of the Invention

The present invention relates to devices in the field of artificial or prosthetic limbs. Specifically, it is a temporary pylon for a below-the-knee amputee. The invention is constructed so as to allow the user to be free from the use of crutches.

2. Description of the Prior Art

The following listed U.S. Patents are found to be the most related to the present invention without disclosing it, either singly or in combination.

| U.S. Pat. No. | Inventor |
| --- | --- |
| 875,482 | Wyatt |
| 2,678,054 | Bostelman |
| 3,016,060 | Beattie, Sr. |
| 4,141,375 | Tykwinski |
| 4,291,715 | Monte |

U.S. Pat. No. 875,482 issued to Wyatt discloses an artificial limb which attaches at the knee and thigh and which includes a support cradle, an elongated outer extension, an inner brace and several adjustments to adapt the limb to the wearer.

U.S. Pat. No. 2,678,054 issued to Bostelman discloses an adjustable crutch having an elongated staff, a leg cradle and a diagonal brace to support it, the crutch being useful to a person with an injury below the knee.

U.S. Pat. No. 3,016,060 issued to Beattie, Sr. discloses a riding crutch for amputees which has a seat member for supporting the user, a single tubular leg and an elongated upper member with an armrest.

U.S. Pat. No. 4,141,375 issued to Tykwinski discloses a knee crutch-cane having a single tubular leg, a support cradle for the leg and an elongated handle. The crutch-cane can be folded for ease of storage.

U.S. Pat. No. 4,291,715 issued to Monte discloses a foot support, crutch with a cushion support for the leg, a ground support member and an elongated support with an arm piece. The body weight is carried by the cushion support, through the ground support member.

Of the above U.S. Patents, the Wyatt patent discloses the device closest to the present invention. Note however that it is not secured to the waist of the wearer nor is it contoured for a comfortable fit for the wearer. The side frame in the Wyatt device does not extend upward enough to allow this.

SUMMARY OF THE INVENTION

By the present invention, an improved temporary pylon for below-the-knee amputees is provided. The invention provides for a femoral/knee containment contour frame that is pre-shaped to the user's knee and thigh contour. A containment holder is provided to secure the leg in the containment frame. To secure the device to the body a waist belt is provided, serving to eliminate the need for crutches. A knee plate covered with a kneepad is positioned at the bottom of the containment frame.

To provide for easy storage and travel, ground support tubing is detachable from the underside of the containment frame. A conventional rubber crutch tip is provided at the end of the tubing. The tip can be rotated in order to provide maneuverability to the user.

Accordingly, one of the objects of the present invention is to provide a temporary pylon for below-the-knee amputees that has a pre-shaped femoral and knee containment frame to fit the user's contours, allowing for a certain degree of comfort.

Another object of the invention is to provide a temporary pylon that does not require the use of crutches, allowing the user freedom of arm and hand movement.

A still further object of the present invention is to provide a portable and easily stored prosthetic device for traveling.

Yet another object of the present invention is to allow the user additional maneuverability in turning the body.

These and other additional objects will be readily apparent after review of the following attached specification, drawings and claims.

BRIEF DESCRIPTION OF THE DRAWINGS

Like reference numerals refer to similar features throughout the drawings and specification.

DETAILED DESCRIPTION OF THE PREFERRED EMBODIMENT

Figure 1:
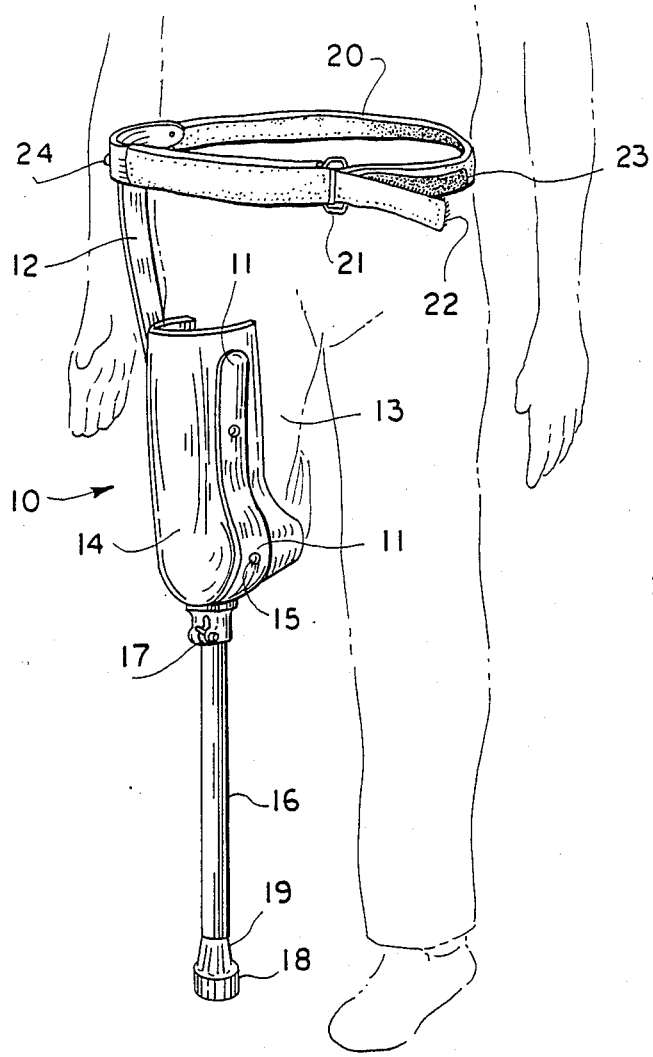
FIG. 1 shows a front perspective view of a user wearing the temporary pylon.

The temporary pylon 10 includes two contoured aluminum frame members 11,12 that would be on either side of the wearer's thigh 13. Affixed in-between these two frame members is a pre-shaped contoured cradle 14, made of plastic, in which the wearer's knee and thigh would be placed in a bent position. The cradle 14 is pre-shaped, from a cast taken of the wearer, to the distinct size contours and lines of the wearer's knee and thigh 13 so as to provide the most comfort in use. Fasteners 15 hold the cradle 14 onto the frame members 11,12. The inside of the cradle 14 could be provided with a layer of padding (not shown) so as to cushion the wearer's knee.

Attached to the bottom of the contoured frame members 11,12 is a length of detachable aluminum support tubing 16 with a lockable clamp assembly 17 to hold in tubing 16. Attached to the bottom end of support tubing 16 is a rubber crutch tip 18. The crutch tip 18 can be provided with a rotatable joint 19 attached to tubing 16 to allow maximum stationary turning movement for the wearer. The joint 19 can be a ball or roller bearing assembly.

The upper end of frame member 12 is attached to a waist belt 20. The belt 20, made of leather or synthetic web such as a safety belt would be made out of, allows the prosthetic leg 10 to be worn without the aid of crutches. Included is a typical adjustment buckle 21 and a VELCRO or other suitable fastener 22,23. A swivel 24 allows the frame members 11,12 to pivot as the wearer walks. The leg assembly as a whole provides maximum comfort and freedom for the wearer.

Figure 2:
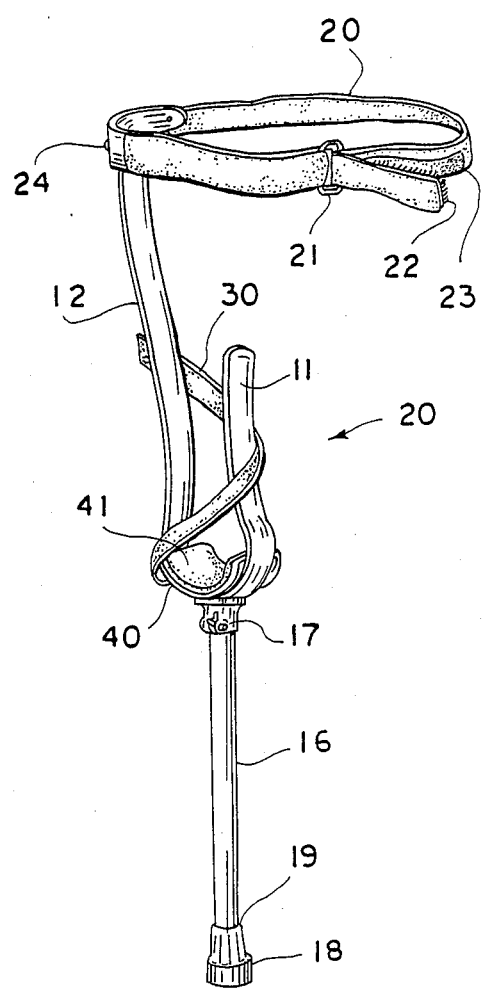
FIG. 2 shows a front perspective view of an alternate embodiment of the device.

An alternate embodiment 20 is shown in FIG. 2. A simpler design is presented here. The cradle 14 of the first embodiment in FIG. 1 is absent. A wraparound strap 30 made of gum rubber or elastic webbing is provided as a containment device, the strap 30 having VELCRO fasteners as does the outside of frame member 12 (not shown). The strap 30 is wrapped tightly around the thigh and frame members 11,12 and the strap 30 fastened to the outside of the frame member 12. An aluminum plate 40 with attached padding 41 provides comfortable support for the knee of the wearer.

The embodiments described above are not meant to be used as permanent replacements, but as a temporary relief from crutches or a more conventional prosthetic device. They can be used for around the home, short-distance walks, or at the work place.

It is to be understood that the present invention is not limited to the sole embodiments described above, but encompasses any and all embodiments within the scope of the following claims.

I claim:

1. A temporary pylon for a below knee amputee comprising:
   a frame structure comprising inner and outer frame members, said frame members extending vertically up at either side of a wearer's knee and thigh, said outer frame member extending to a wearer's waist, said frame members being contoured to the shape of a wearer's thigh;
   a containment means to hold a wearer's knee and thigh between said frame members;
   a support means detachably affixed to the bottom of said frame structure and extending downward to the ground, allowing the wearer to stand; and
   a securing means comprising an adjustable belt wrapped around the waist of the wearer to secure the temporary pylon to the wearer, said outer frame member pivotally affixed to said belt, whereby
   said extended outer frame member and said pivoted waist belt serve to increase the stability and rigidity of the pylon and to keep the leg of the wearer aligned with the pylon.

2. The temporary pylon according to claim 1, wherein said containment means comprises a pre-shaped, contoured, one piece cradle that substantially surrounds and envelopes the wearer's knee and thigh, said cradle disposed and affixed between said frame members.

3. The temporary pylon according to claim 1, wherein said containment means comprises a wrap-around strap, said strap wrapping around said frame members with the wearer's knee and high disposed between said frame members; and
   said strap removably fastenable to said frame members to secure the temporary pylon to the wearer's knee and thigh.

4. The temporary pylon according to claim 3, including:
   a contoured plate affixed atop said support means between the bottom of said frame members; and
   padding affixed atop said plate to cushion the wearer's knee.

5. The temporary pylon according to claim 1, wherein said support means comprises a length of tubing, said tubing removably affixed to said frame structure by a locking clamp.

6. The temporary pylon according to claim 5, including:
   a crutch tip disposed on the bottom of said tubing; and
   a rotatable joint between said crutch tip and said tubing.

* * * * *